(12) United States Patent
Hasegawa (10) Patent No.: US 9,798,796 B2
(45) Date of Patent: Oct. 24, 2017

(54) RANKING DEVICE, RANKING METHOD, AND PROGRAM

(71) Applicant: National Institute of Advanced Industrial Science and Technology, Chiyoda-ku (JP)

(72) Inventor: Ryohei Hasegawa, Tsukuba (JP)

(73) Assignee: National Institute of Advanced Industrial Science and Technology, Tokyo (JP)

(*) Notice: Subject to any disclaimer, the term of this patent is extended or adjusted under 35 U.S.C. 154(b) by 335 days.

(21) Appl. No.: 14/380,955

(22) PCT Filed: Oct. 12, 2012

(86) PCT No.: PCT/JP2012/076518
§ 371 (c)(1),
(2) Date: Aug. 26, 2014

(87) PCT Pub. No.: WO2013/128701
PCT Pub. Date: Sep. 6, 2013

(65) Prior Publication Data
US 2015/0026195 A1    Jan. 22, 2015

(30) Foreign Application Priority Data

Feb. 28, 2012 (JP) ................................. 2012-040913

(51) Int. Cl.
*G06F 17/30* (2006.01)
*A61B 5/0476* (2006.01)
(Continued)

(52) U.S. Cl.
CPC ...... *G06F 17/30595* (2013.01); *A61B 5/0476* (2013.01); *A61B 5/04842* (2013.01); *G06F 19/36* (2013.01); *G06Q 30/02* (2013.01)

(58) Field of Classification Search
CPC .... G06F 17/30595; G06F 17/30; G06F 19/36; G06F 19/20; G06Q 30/02;
(Continued)

(56) References Cited

U.S. PATENT DOCUMENTS

| 5,406,956 A * | 4/1995 | Farwell | A61B 5/0478 600/544 |
| 7,010,167 B1 * | 3/2006 | Ordowski | G06K 9/6267 345/644 |

(Continued)

FOREIGN PATENT DOCUMENTS

| JP | 2004029961 | 1/2004 |
| JP | 2010042236 | 2/2010 |

(Continued)

OTHER PUBLICATIONS

"International Application No. PCT/JP2012/076518, International Search Report dated Nov. 27, 2012", (Nov. 27, 2012), 5 pgs.

(Continued)

*Primary Examiner* — Anh Ly
(74) *Attorney, Agent, or Firm* — Schwegman Lundberg & Woessner, P.A.

(57) ABSTRACT

A device, a system, a method, and a program are realized which are capable of predicting the order of the feeling and the preference of a subject to products which are the research objects, for marketing research and others. The images of a plurality of research objects are presented a plurality of times as visual stimuli in order to measure the brain wave. A brain wave data of an event related electrical potential for the research objects which the subject has selected as a target immediately after the stimulus presentation, is processed by a linear discriminant analysis to quantitatively represent with a single index, in order to rank the research objects.

3 Claims, 6 Drawing Sheets

(51) Int. Cl.
  *G06Q 30/02* (2012.01)
  *A61B 5/0484* (2006.01)
  *G06F 19/00* (2011.01)
(58) Field of Classification Search
  CPC .............. G06Q 30/0241; A61B 5/0476; A61B 5/04842; A61B 5/04845; A61B 5/0484; A61B 5/4076; G09B 7/00; G09B 7/073; G09B 23/28; G06K 9/00496
  See application file for complete search history.

(56) References Cited

U.S. PATENT DOCUMENTS

| | | | |
|---|---|---|---|
| 8,473,345 B2 | 6/2013 | Pradeep et al. | |
| 8,484,081 B2 | 7/2013 | Pradeep et al. | |
| 2002/0188217 A1* | 12/2002 | Farwell | A61B 5/164 600/544 |
| 2004/0243328 A1* | 12/2004 | Rapp | A61B 5/4094 702/71 |
| 2005/0143629 A1* | 6/2005 | Farwell | A61B 5/4035 600/300 |
| 2006/0114222 A1 | 6/2006 | Araki et al. | |
| 2006/0193518 A1* | 8/2006 | Dong | G06K 9/00859 382/186 |
| 2006/0217781 A1* | 9/2006 | John | A61N 1/36017 607/45 |
| 2007/0173733 A1* | 7/2007 | Le | G06F 19/363 600/544 |
| 2008/0071136 A1* | 3/2008 | Oohashi | A61M 21/02 600/27 |
| 2008/0091762 A1* | 4/2008 | Neuhauser | G06F 19/327 709/201 |
| 2008/0166707 A1* | 7/2008 | Han | C12Q 1/6827 435/6.14 |
| 2008/0208072 A1* | 8/2008 | Fadem | A61B 5/0484 600/544 |
| 2008/0255949 A1* | 10/2008 | Genco | A61B 5/0205 705/14.4 |
| 2009/0012766 A1* | 1/2009 | Miyake | G06F 19/20 703/11 |
| 2009/0297000 A1* | 12/2009 | Shahaf | G06K 9/00543 382/128 |
| 2009/0318773 A1* | 12/2009 | Jung | A61B 5/04009 600/300 |
| 2010/0094378 A1* | 4/2010 | Inui | A61B 5/04001 607/46 |
| 2011/0307030 A1* | 12/2011 | John | A61N 1/36103 607/45 |
| 2012/0296569 A1* | 11/2012 | Shahaf | A61B 5/048 702/19 |
| 2014/0082244 A1* | 3/2014 | Liu | G06F 13/24 710/268 |
| 2014/0163328 A1* | 6/2014 | Geva | A61B 5/048 600/300 |
| 2014/0276183 A1* | 9/2014 | Badower | A61B 5/0476 600/544 |
| 2014/0347265 A1* | 11/2014 | Aimone | G09G 3/003 345/156 |
| 2015/0313496 A1* | 11/2015 | Connor | A61B 5/0476 600/301 |
| 2016/0239084 A1* | 8/2016 | Connor | A61B 5/0478 600/544 |
| 2016/0242690 A1* | 8/2016 | Principe | A61B 5/742 600/544 |
| 2017/0120043 A1* | 5/2017 | John | A61N 1/0534 607/45 |

FOREIGN PATENT DOCUMENTS

| | | |
|---|---|---|
| JP | 2010522941 | 7/2010 |
| JP | 2010274035 | 12/2010 |
| JP | 2011013871 | 1/2011 |
| JP | 2011120824 | 6/2011 |
| WO | WO-2006003901 | 1/2006 |
| WO | WO-2013128701 | 9/2013 |

OTHER PUBLICATIONS

McClure, Samuel M., et al., "Neural Correlates of Behavioral Preference for Culturally Familiar Drinks", Neuron, vol. 44, 379-387, (Oct. 14, 2004), 379-387.

Tanaka, Motoshi, et al., "Measurements of Event-Related Potential for Opinion Test of Food with Their Pictures", The Institute of Electronics, Information and Communication Engineers, IEICE Technical Report, NC2009-52 (Nov. 2009), vol. 109, No. 280, p. 13-18, (Nov. 5, 2009), 13-18.

"Japanese Application Serial No. 2012-040913, Office Action dated Feb. 9, 2016", (w/ English Translation), 7 pgs.

"International Application No. PCT/JP2012/076518, International Preliminary Report for Patentability dated Sep. 12, 2014", (w/ English Translation), 11 pgs.

"International Application No. PCT/JP2012/076518, Written Opinion dated Nov. 27, 2012", (w/ English Translation), 7 pgs.

"Japanese Application Serial No. 2012-040914, Office Action dated Jul. 7, 2015", (w/ English Summary), 5 pgs.

"Machine Translation of JP 2004-029961A, published Jan. 29, 2004", 53 pgs.

"Machine Translation of JP 2010-042236A, published Feb. 25, 2010", 30 pgs.

* cited by examiner

RANKING DEVICE, RANKING METHOD, AND PROGRAM

TECHNICAL FIELD

The present invention relates to a device, a system, a method, and a program for ranking the intensity of responsiveness of a brain to external stimulus options.

BACKGROUND ART

Conventionally, the questionnaire research, which is one of the main means of the market research that has been carried out for product development and sales strategy, occasionally has had problems in the accuracy and reliability of the research result due to the bias of the conscious and unconscious minds of the respondents. In recent years, the brain activity analysis related to the consumer behavior and the marketing research method based on the brain activity have been developed actively. For example, there is known a study for identifying the brain part relevant to preferential inclination and brand consciousness by the brain activity measuring experiment using a large-sized device called fMRI, and a study for researching the difference of brain activity by the power of brand (refer to Non Patent Literature 1).

The study group of the present inventor has already proposed an opinion communication method utilizing the brain wave, and the method called "brain information map" which presents the brain information expression to the external event with a map (refer to Patent Literatures 1 and 2).

Recently, the marketing that focuses on a brain wave is under development (refer to Patent Literatures 3 and 4).

CITATION LIST

Patent Literature

Patent Literature 1: Japanese Patent Laid-Open No. 2010-274035
Patent Literature 2: Japanese Patent Laid-Open No. 2011-013871
Patent Literature 2: National Publication of International Patent Application No. 2010-522941
Patent Literature 3: Japanese Patent Laid-Open No. 2011-120824

Non Patent Literature

Non Patent Literature 1: McClure S M et al, "Neural Correlates of Behavioral Preference for Culturally Familiar Drinks" Neuron 44, p 379-387, 2004

SUMMARY OF INVENTION

Technical Problem

As a conventional technology which focused on a brain wave, there is a technology for giving a meaning to the brain wave by researching the correlation between an evaluation result of a questionnaire and the brain wave with respect to various emotion types such as comfort or discomfort, which is obtained by the questionnaire sheet. In this technology, if the correlation between the brain wave and each emotion type is high, the intensity of each emotion can be estimated from the brain wave to a certain extent. On the other hand, if the correlation is low, there is a problem of the low probability that the emotion is estimated from the brain wave correctly. Also, although the logic "when the brain wave of this kind is observed, the emotional state is generally like this" is used based on the database of a large number of subjects, the fact that the pattern of the brain wave for each subject has variations even within the normal limits is disregarded, and it is questioned whether or not the data analysis conducted is scientifically meaningful. Further, in the first place, the meaning of taking the trouble to extract from the brain wave the information that is understandable from the questionnaire sheet is not clear.

Patent Literature 1 discloses a brain information map aiming at conducting a feeling evaluation from which the subjective bias of the subject is eliminated. In the application utilizing the map, the map visualization is generated with respect to how the brain activity including both of the conscious mind and the subconscious mind expresses to a large number of product pictures and the like, from the similarity among the brain waves of individuals (without conducting a questionnaire research). Although this technology is significantly meaningful in avoiding the problem of "the tautology of brain wave and subjective emotion" (that is, if only the subjective consciousness is referred to interpret the meaning of the brain wave data, only the deviation having a high correlation with the subjective consciousness can be interpreted after all; then, asking a questionnaire as to the subjective conscious state is more accurate than analyzing the brain wave), the map information alone cannot directly answer the question "Is it possible to predict which product will be bought in future?" which is an important challenge in the marketing. Therefore, the remaining challenge is construing the brain information that leads to the final purchase action, regardless of the subjectivity of the subject.

The present invention is to solve these problems, and has a purpose of determining the difference in the degree of the rising attention of the subject to each research object by analyzing the brain wave for ranking. For example, the present invention has a purpose of predicting the order of the popularity of the products which are the research objects, in the prediction of the purchase action of a marketing research. In the marketing field, the research object is not limited to the products, but includes brands, characters, advertisements, and the like. The present invention has a purpose of giving a specific order to rank the information of the brain activity including both of the conscious mind and the subconscious mind, such as opinion, feeling, preference, and the like of the subject, not only in the marketing field, but in the entertainment field, the medical and health field, the educational and amusement field, and others.

Solution to Problem

To achieve the above purposes, the present invention focuses attention on the brain activity reflecting the rise of the attention which is considered to be important for the prediction of the purchase action, particularly, the event related electrical potential which is a kind of the brain wave recorded on the scalp, in order to conduct ranking of the responsiveness of the brain to the products which are the research object. Specifically, the present invention includes three processes: brain wave measurement, visual stimulus presentation experiment, and data analysis. The present invention construes which product causes the highest responsiveness of the brain, i.e., which product arouses the attention most including the subconscious mind, and the order of the aroused attention.

To achieve the purposes, the present invention has the following features.

The device of the present invention is a device for ranking a plurality of research objects, configured to execute an analytical process to quantitatively represent, with a single index, brain wave data of event related electrical potentials when each of the research objects is selected as a target, to rank the research objects. The analytical process can employ a pattern classification method. The analytical process can employ a discriminant analysis. The analytical process can employ a linear discriminant analysis. A preferable example of the single index is a discriminant point of the discriminant analysis.

In the present invention, the brain wave data that is subjected to the analytical process is the brain wave data of the event related electrical potential. In the present invention, the brain wave data that is subjected to the analytical process includes at least the brain wave data of the event related electrical potential when the research object is selected as the "target".

The system of the present invention is a system for ranking a plurality of research objects, comprising: a stimulus presentation device configured to present stimuli; a brain wave monitor; and a processing device configured to process brain wave data from the brain wave monitor, wherein the stimulus presentation device presents a plurality of research objects as the stimuli a plurality of times, wherein the brain wave monitor measures brain waves immediately after the stimuli are presented by the stimulus presentation device, wherein the processing device executes an analytical process to quantitatively represent, with a single index, the measured brain wave data (a change contained in the brain wave data cut out by timing such as stimulus presentation is generally referred to as an event related electrical potential), to rank the research objects. The event related electrical potential includes at least the event related electrical potential when each research object is selected as the target.

The method of the present invention is a method for ranking a plurality of research objects, comprising quantitatively representing, with a single index, brain wave data of event related electrical potentials, to rank the research objects. The event related electrical potential includes at least the event related electrical potential when each research object is selected as the target.

The program of the present invention is a program for causing a computer to function as: stimulus presentation means for presenting a plurality of research objects as stimuli, a plurality of times for each research object; process means for executing an analytical process to quantitatively represent, with a single index, brain wave data of event related electrical potentials immediately after the stimulus presentation, to rank the research objects; and presentation means for presenting a ranking result. The event related electrical potential includes at least the event related electrical potential when each research object is selected as the target.

Advantageous Effects of Invention

According to the present invention, only by analyzing the event related electrical potentials for a plurality of research objects, the responses of the subject to the plurality of research objects are immediately ranked, so that the brain information is objectively construed. According to the present invention, the subject himself/herself does not select the "target", but works only to find the target specified by the experimenter, so that the possibility of receiving a subjective influence becomes extremely low advantageously.

According to the present invention, for example, the experiment is finished within five to ten minutes for eight product types, even if the analysis is conducted for each subject. The difference of the discriminant point sometimes occurs by chance. In that case, its possibility can be verified by the statistical verification. Because the experimental result can promptly be fed back to the subject, the product selection can be made with reference to the subject's own activity of the brain, to support the opinion decision.

By the ranking of the present invention, the order of the popularity of the products which are the research objects is predicted in the prediction of the purchase action of the marketing research. The research object is not limited to the products, but includes brands, characters, advertisements, and others. Also, the present invention can be utilized in various researches such as the prediction of success or failure in election. Also, the present invention can objectively present the information of the brain activity including both of the conscious mind and the subconscious mind, such as opinion, feeling, preference, and the like of the subject, not only in the marketing field, but in the entertainment field, the medical and health field, the educational and amusement field, and others, eliminating the bias of the conscious and unconscious minds of the subject which can be a problem in a questionnaire research and the like.

With the ranking of the present invention, the present invention can also be utilized as an opinion communication support device in the welfare field.

DESCRIPTION OF EMBODIMENTS

The present invention will be described with an embodiment.

First Embodiment

Figure 1:
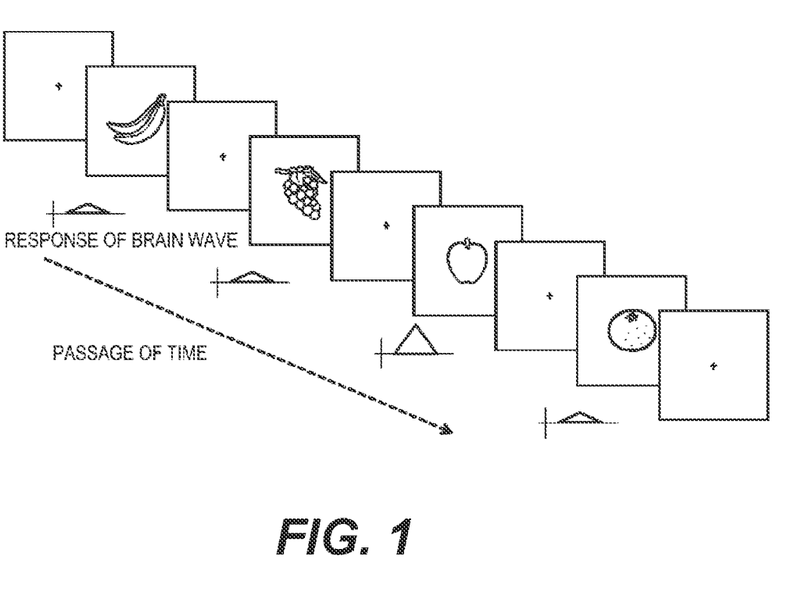
FIG. 1 is a diagram illustrating a first embodiment schematically.
Figure 2:
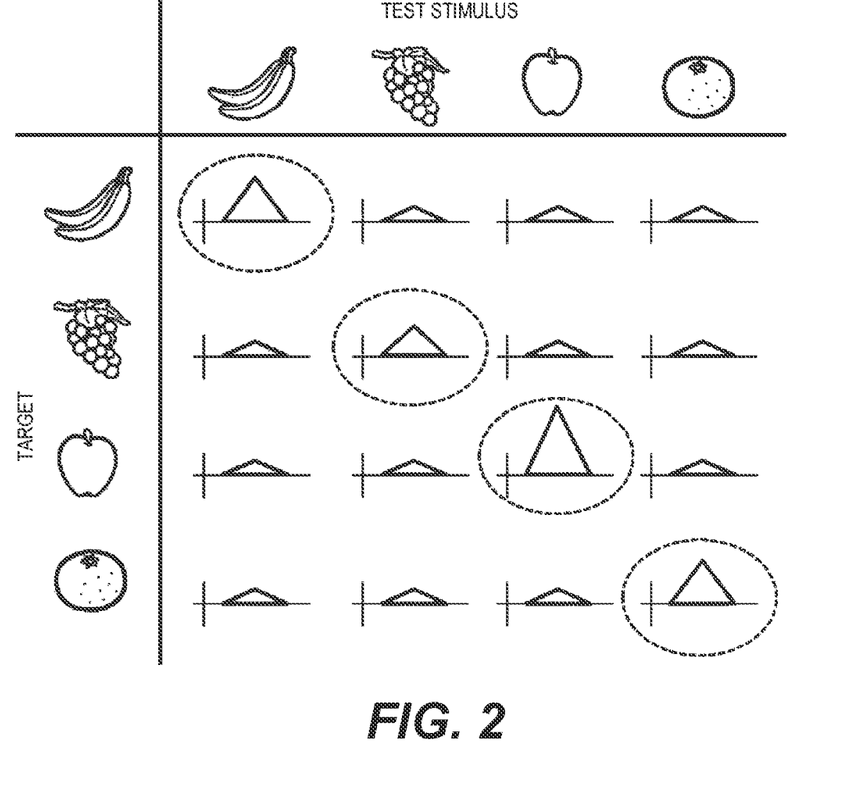
FIG. 2 is a diagram illustrating brain waves schematically for describing the first embodiment.

The present embodiment will be described below with reference to FIGS. 1 to 5. FIG. 1 is a diagram which schematically illustrates presentation of stimulus events, and the response of the brain wave of a subject to the presentation, in the present embodiment. As illustrated in FIG. 1, the stimulus events (also referred to as attention arousing events), for example pictures, are presented to the subject via the display one event (one sheet) at a time, and the brain wave of the subject who watches the event is measured by a brain wave monitor with electrodes attached on the head of the subject, and the brain wave is analyzed by a brain wave analysis processing device such as a computer. The stimulus event is a research object itself, a picture of the research object, or the like. FIG. 2 schematically illustrates the brain waves with respect to a plurality of stimulus events, for describing the present embodiment. Specifically, the present invention is implemented by conducting (A) brain wave measurement with respect to test stimuli, and (B) analytical process and ranking process of brain wave data, as below.

(A) Brain Wave Measurement with Respect to Test Stimuli

The brain wave from a single or a plurality of electrodes provided on the scalp around the center at the top of the head is measured. The measurement is conducted in the following procedure.

(1) Visual stimuli (picture, illustration, and the like of research objects) relevant to the products which are various research objects to be compared are presented to the subject. For example, the visual stimuli (fruits are illustrated in FIG. 1) are continually presented on the screen of a computer or the like, like a picture-card show, in a pseudorandom order. (Refer to FIG. 1)

(2) In doing so, the subject is informed of one (for example, banana) of the product group (a plurality of fruits (banana, grape, apple, orange) in FIG. 1) as a "target". Each visual stimulus is presented a plurality of times, and the subject is instructed and made to count, in the mind, the number of presentation only for the stimulus of the target.

(3) With the intervals of short break, the above (2) is carried out by changing the information of the "target" one after another, so as to be carried out for all the products, which are options, as the "target".

The above (2) and (3) are described in more detail. For example, a banana is set as the "target" of the first time, a grape is set as the "target" of the second time, an apple is set as the "target" of the third time, and an orange is set as the "target" of the fourth time. Then, for all the product pictures, the brain wave data for the product picture set as the target, and the brain wave data for the product picture not set as the target are acquired. In FIG. 2, the acquired responses of the brain waves are schematically illustrated. The first row of the brain wave data of FIG. 2 is the brain wave data corresponding to each test stimulus when the subject is informed of the banana as the "target" and made to count in viewing the product group. As illustrated schematically, among the brain wave data of the first row, the brain wave data for the test stimulus of the target (banana) has a larger response of the brain wave than the brain wave data for the test stimuli of the non-targets (grape, apple, orange). Likewise, also in each row from the second row to the fourth row, among the brain wave data, the brain wave data (the brain wave encircled by the dotted line) for the test stimulus of the target has a larger response of the brain wave than the brain wave data for the test stimuli of the non-targets.

The present inventor focused attention on the fact that the brain wave data for the test stimuli of the targets (the brain waves encircled by the dotted line) are different from each other (refer to FIG. 2), and quantified and discriminated the brain wave data (the brain wave encircled by the dotted line) for the test stimulus of the target in order to rank the test stimulus objects.

Although the research objects have been illustrated simply with an example of fruits, a plurality of test stimuli of other kind have been tried. First, the experiment as in FIG. 1 is carried out for the number of the products which are options. When the target is changed in each experiment, each experiment normally records the highest response of the brain wave (the event related electrical potential) for the "target". However, the height of the electrical potential has a slight difference depending on which product is the target. In the difference, the difference of the aroused attention to each product of the subject (the intensity of the conscious and subconscious interests) is considered to be reflected.

Here, the brain wave for the test stimulus is described. The present embodiment utilizes the brain wave electrical potential, which is called the event related electrical potential (or referred to as an event related brain wave), for the test stimulus. The event related electrical potential is a transient brain wave that arises in time with the generation timing of the external or internal event and affects the cognitive process, and includes P300 (the electropositive potential change 300 milliseconds after the stimulus presentation) and the like.

Figure 3:
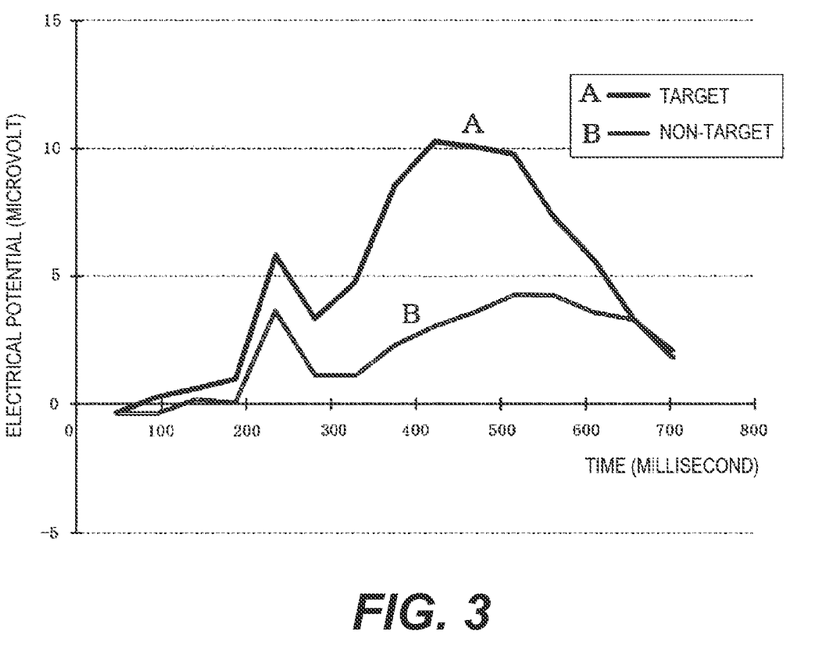
FIG. 3 is a diagram illustrating examples of event related electrical potentials.

FIG. 3 schematically illustrates an example of the event related electrical potential. The curving line A shows the brain wave when the test stimulus object (for example, a picture) is cautiously watched and selected (when selected with the target in mind under the condition for actively searching the target (i.e., by selecting or searching with the target and the non-target in mind)), and is an example of the brain wave for the above "target". The curving line B shows the brain wave when the test stimulus object is cautiously watched but not selected (when not selected with the non-target in mind), and is an example of the brain wave for the above "non-target".

Figure 4:
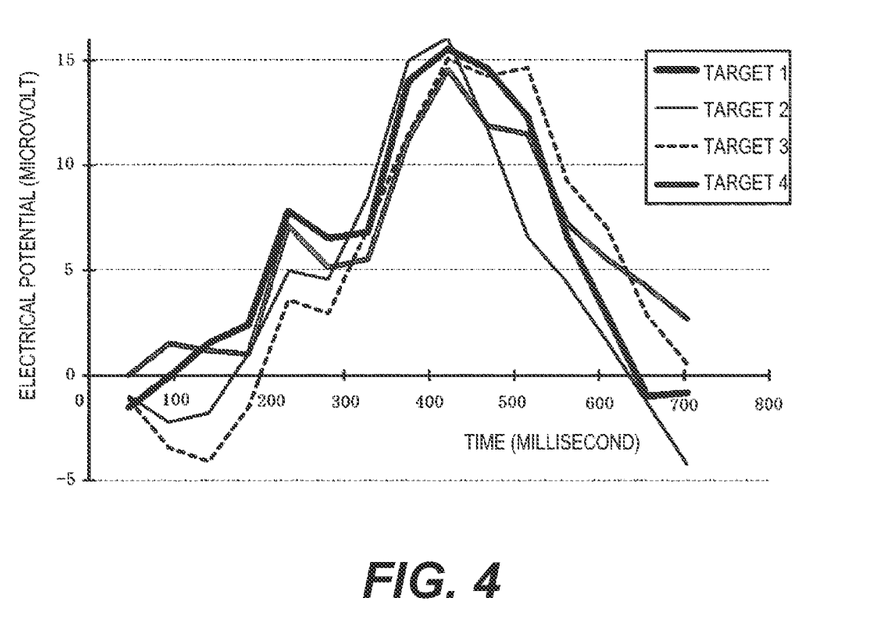
FIG. 4 is a diagram illustrating event related electrical potentials with respect to targets, for the respective targets.

FIG. 4 schematically illustrates the brain waves (the event related electrical potentials) for the "targets", for the respective targets. The event related electrical potentials varies depending on which product (targets 1, 2, 3, 4) is the target.

(B) Analytical Process and Ranking Process of Brain Wave Data

In the present invention, the difference of the aroused attention, and the intensity of the conscious and subconscious interests are represented quantitatively to rank each product (object). In the present embodiment, a discriminant analysis method is utilized to represent the intensity of the response with one index. Other pattern classification methods and the like can be used for quantitative expression.

Figure 5:
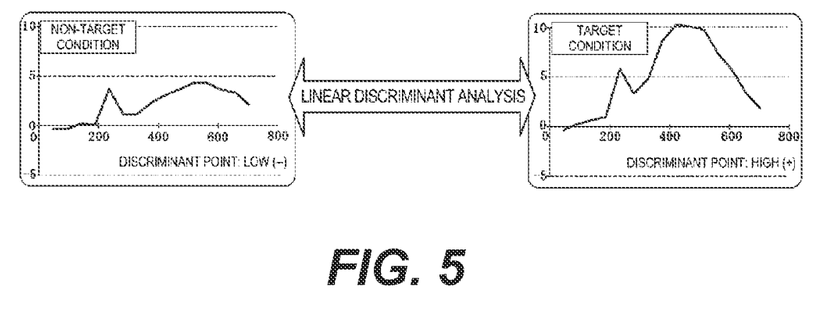
FIG. 5 is a diagram for describing a linear discriminant analysis of the first embodiment.

In the present embodiment, the discriminant analysis is conducted in two classifications of the "target" and the "non-target" for all experimental data to produce a discriminant model equation 602 (See FIG. 6), and thereafter a discriminant point for each product is calculated 604 (See FIG. 6), in order to quantitatively represent the difference of the aroused attention, and the intensity of the conscious and subconscious interests. FIG. 5 is a diagram for schematically describing a linear discriminant analysis. The brain wave when selecting with the target in mind (target condition) is illustrated at right, and the brain wave when not selecting with the non-target in mind (non-target condition) is illustrated at left. The linear discriminant analysis is conducted for all the data with respect to which waveform is more similar, and the discriminant point for each product is calculated.

The analytical process and the ranking process of the brain wave data mainly include the following procedures.

(1) The multivariate brain wave data acquired by the execution of the above (A) are classified into those for the "target" and those for the "non-target", and a pattern classification method such as the linear discriminant analysis is carried out to decide the weighting of the discriminant model equation.

(2) The average value of the discriminant points when each product is the target is calculated using the acquired discriminant equation.

Figure 6:
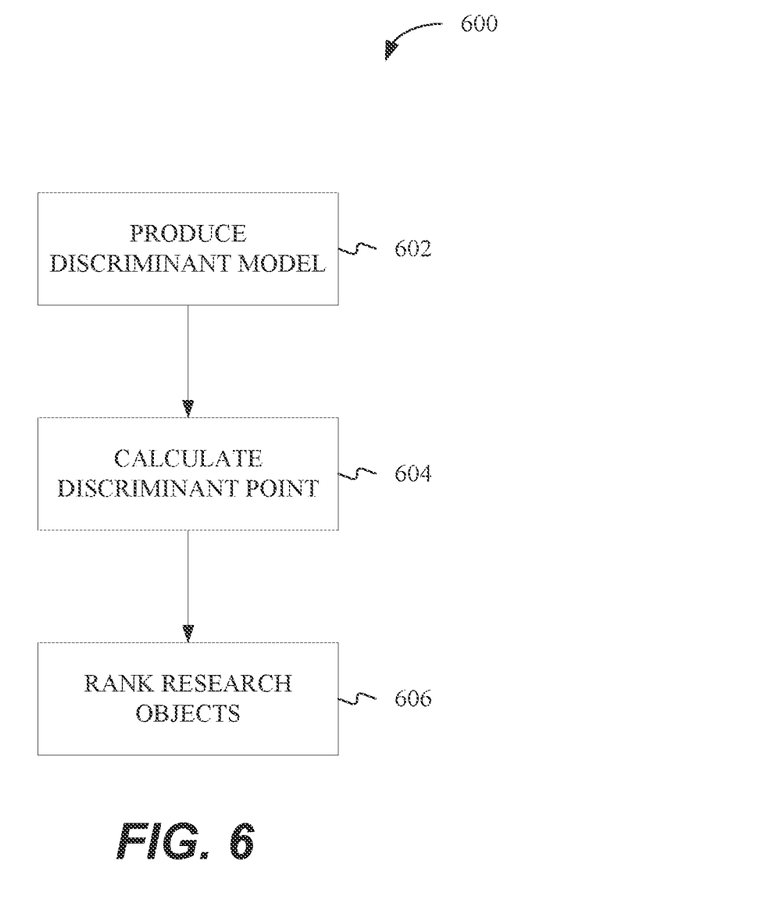
FIG. 6 is a flowchart.

(3) The average value of the discriminant points is compared between the products to rank the products in the order of the discriminant point 606 (See FIG. 6).

In carrying out the above (1), (2) and (3), the followings are carried out, for example.

(a) First, the verification with respect to whether or not the experiment is properly conducted is confirmed by that "the average value of the response of the brain wave for the target stimulus is larger than the average value of the response for the non-target stimulus" (refer to FIG. 3).

(b) Then, whether or not the response varies depending on the difference of the visual stimulus which is the target is confirmed by "graphically showing the responses of the brain wave for the target stimuli for each of the stimuli" (refer to FIG. 4). Note that, since the data is secured multiple times (for example, five to ten times) for each target stimulus, when showing graphically, the arithmetic mean is calculated for each stimulus and for each data point of the time-series data.

(c) Then, the discriminant point (y) for one presentation of each image (visual stimulus) is calculated by the linear discriminant function represented by the below equation (Expression 1).

$$y = \sum_{i}^{n} w_i x_i + c \quad \text{[Expression 1]}$$

In the equation (Expression 1), x is the value of the brain wave data (voltage) of a certain channel at a certain time point. With regard to the types of x, there exist types (n) calculated by multiplying the data point with the number of the channel (the number of the channel according to the number of the measurement positions, because the brain wave data is acquired at a plurality of the measurement positions on the scalp of the head of the subject). The weighting factor w and the constant term c for each brain wave data are able to be calculated by the linear discriminant analysis. Although it is desirable that the data of a "training session" (the experiment conducted in the condition same as or similar to the main experiment) conducted before the experiment for calculating the discriminant point be used as the object on which the linear discriminant analysis is conducted, the experimental data itself using the data of the experiment for which the discriminant point is to be calculated may be used.

(d) By using the above method, the discriminant points are added for each image, for the number of times of the stimulus presentation (which is identical for all images). Or, the arithmetic mean may be calculated. Usually, it is confirmed that the discriminant point (the summation value or the arithmetic mean value) for the image which is the "target" is higher than the points of the remaining "non-target" image group in a certain experimental session.

(e) As described above, the experimental session is repeated such that all the images respectively become the "target". After all the experimental sessions are finished, the summation values (or the arithmetic mean values) of the discriminant points when the respective images become the "target" are compared and lined up in the order from high points in order to conduct ranking.

(f) Note that, since the data is secured multiple times (five to ten times) for each target stimulus, as many of the discriminant points as the number of the times exist for the same stimulus, and whether or not the difference between the stimuli is significant can be confirmed by a statistical verification (ANOVA or the like).

Note that, not only for the event related electrical potential when selecting as the "target", but also for the event related electrical potential when not selecting with the "non-target" in mind in the above experiment, the same process of the event related electrical potential can be conducted, to acquire the discriminant point and conduct the ranking process.

In the embodiment, the image has been taken as an example to describe the visual stimulus, but the auditory stimulus or others may be provided instead of the visual stimulus to measure and analyze the corresponding brain wave. Also, with regard to the ranked result, the product of the object may be displayed on the display means such as a display or the like, or may be informed with sound.

Also, the present invention can be utilized for multiple research objects, and is advantageous for three or more, or further larger number of the research objects. For example, for eight product types, each subject is finished with measurement of the brain wave for about five to ten minutes, and the brain wave data analysis and the ranking process for about three to five minutes, and therefore the marketing research is finished simply and in a short time. With regard to the ranking of the result of the experiment, the same results were obtained for the same subject in the multiple experiments. Also, the ranking was similar to the actual preference of the subject.

By carrying out the present invention, the opinion, the preference, the unconscious impression and feeling information, and others of the subject to the research objects can be grasped objectively. Also, by informing the subject himself/herself of the result, the result can be fed back to the opinion decision of the subject himself/herself. The research objects may be the illustration of the message used for opinion communication support in the welfare field, in addition to the objects of the conventional marketing research.

Note that the examples illustrated in the above embodiment, etc., are described to facilitate the understanding of the invention, and are not limited to the embodiment.

INDUSTRIAL APPLICABILITY

According to the present invention, the unconscious impression and feeling information and the like, which are difficult to measure in a questionnaire research susceptible to the influence of the conscious bias, can be ranked in an easily understandable manner using the brain activity as an index, and be referred to for development of a new product and the like. Also, in the welfare field, the present invention can be used as an opinion communication support device, by using an illustration of a message to be conveyed or the like, instead of a product picture.

The invention claimed is:

1. A ranking device for ranking a plurality of research objects based on differences in a degree of a rising attention of a subject to each of the plurality of research objects, configured to:

classify target and non-target for brain wave data of event related electrical potentials, wherein the brain wave data is measured by a brain wave monitor with electrodes attached on a head of the subject;

calculate a weighting factor of discriminant equation based on data point of time series data and the number of a channel according to a number of measured positions where the brain wave data of the even related electrical potential is acquired when each of the plurality of research objects is the target;

calculate a discriminant point for each product as the target based on the discriminant equation; and rank the research objects based on the discriminant point calculated for each product.

2. A ranking system for ranking a plurality of research objects based on difference in a degree of a rising attention of a subject to each of the plurality or research objects, comprising:

a stimulus presentation device configured to present stimuli;

a brain wave monitor; and a processing device configured to process brain wave data from the brain wave monitor, wherein the stimulus presentation device presents the plurality of research objects as the stimuli a plurality of times, wherein the brain wave monitor measures brain waves immediately after the stimuli are presented by the stimulus presentation device by electrodes attached on the head of the subject, wherein the processing device classifies target and non-target for brain wave data of event related electrical potentials, calculates a weighting factor of discriminant equation based on data point of time series data and the number of a channel according to a number of measured positions where the brain wave data of the event related electrical potential is acquired when each of the plurality of research objects is the target, and calculates a discriminant point for each product as the target based on the discriminant equation, to rank the research objects based on the discriminant point calculated for each product.

3. A ranking method for ranking a plurality of research objects based on differences in the degree of the rising attention of a subject to each research object, comprising:

classifying of target and non-target for brain wave data of event related electrical potentials, wherein the brain wave data is measured by a brain wave monitor with electrodes attached on the head of the subject;

calculating weighting factor of discriminant equation based on data point of time-series data and the number of the channel according to the number of the measurement positions where the brain wave data of the event related electrical potential is acquired when each research object is the target; and calculating a discriminant point for each product as the target, to rank the research objects.

* * * * *